(12) United States Patent
Huang et al.

(10) Patent No.: US 11,600,021 B2
(45) Date of Patent: Mar. 7, 2023

(54) SYSTEM AND METHOD FOR CALIBRATION BETWEEN COORDINATE SYSTEMS OF 3D CAMERA AND MEDICAL IMAGING APPARATUS AND APPLICATION THEREOF

(71) Applicant: GE Precision Healthcare LLC

(72) Inventors: Yu Huang, Beijing (CN); Fanbo Meng, Beijing (CN); Yanran Xu, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 352 days.

(21) Appl. No.: 16/884,757

(22) Filed: May 27, 2020

(65) Prior Publication Data

US 2020/0394821 A1     Dec. 17, 2020

(30) Foreign Application Priority Data

Jun. 12, 2019    (CN) .......................... 201910506016.2

(51) Int. Cl.
*A61B 5/00*      (2006.01)
*A61B 5/055*     (2006.01)
(Continued)

(52) U.S. Cl.
CPC .............. *G06T 7/80* (2017.01); *A61B 5/0035* (2013.01); *A61B 5/0037* (2013.01); *A61B 5/055* (2013.01);
(Continued)

(58) Field of Classification Search
None
See application file for complete search history.

(56) References Cited

U.S. PATENT DOCUMENTS 9,633,435 B2 *   4/2017   Ma ............................ G06T 7/90
10,499,996 B2 * 12/2019   de Almeida Barreto ....................
                                                      G06T 19/006
(Continued)

FOREIGN PATENT DOCUMENTS

CN           104224212 B      7/2019

*Primary Examiner* — Soo Shin

(57) ABSTRACT

The present invention relates to a system and a method for calibration between coordinate systems of a 3D camera and a medical imaging apparatus and an application thereof. The calibration system comprises: a calibration tool arranged on a scanning table, wherein the calibration tool is provided with markers and a reference point, the reference point is aligned with a center of the medical imaging apparatus to serve as an origin of the coordinate system of the medical imaging apparatus, and positions of the markers in the coordinate system of the medical imaging apparatus are calculated according to relative positions of the markers with respect to the reference point; a 3D camera for capturing images of the markers and determining positions of the markers in the coordinate system of the 3D camera based on the captured images; and a calculation device for calculating a calibration matrix using the positions of the markers in the coordinate system of the 3D camera and the positions of the markers in the coordinate system of the medical imaging apparatus, and performing calibration between the coordinate system of the 3D camera and the coordinate system of the medical imaging apparatus using the calibration matrix. The method corresponds to the aforementioned system. The present invention further relates to an application of the calibration and a computer-readable storage medium capable of implementing the method and the application.

16 Claims, 7 Drawing Sheets

(51) Int. Cl.
*A61B 6/00* (2006.01)
*A61B 6/03* (2006.01)
*A61B 6/10* (2006.01)
*G06T 7/73* (2017.01)
*G06T 7/80* (2017.01)
*H04N 13/246* (2018.01)

(52) U.S. Cl.
CPC .............. *G06T 7/73* (2017.01); *H04N 13/246* (2018.05); *A61B 6/102* (2013.01); *A61B 6/488* (2013.01); *A61B 2560/0238* (2013.01); *G06T 2207/10028* (2013.01); *G06T 2207/30196* (2013.01); *G06T 2207/30204* (2013.01); *G06T 2207/30244* (2013.01)

(56) References Cited

U.S. PATENT DOCUMENTS

| | | | | |
|---|---|---|---|---|
| 2008/0097156 A1* | 4/2008 | Nakamura | ............ | A61B 5/062 600/117 |
| 2015/0297177 A1* | 10/2015 | Boctor | ................... | A61B 34/30 901/47 |
| 2017/0091940 A1* | 3/2017 | Ma | ............................ | G06T 7/90 |
| 2017/0100089 A1* | 4/2017 | Chang | .................... | A61B 6/488 |
| 2018/0325415 A1* | 11/2018 | Ehrl | ........................ | G06T 7/246 |
| 2018/0338742 A1* | 11/2018 | Singh | ....................... | A61B 6/40 |
| 2019/0192105 A1* | 6/2019 | Mewes | .................. | A61B 6/032 |
| 2019/0311490 A1* | 10/2019 | Crawford | ............... | A61B 6/102 |
| 2021/0201476 A1* | 7/2021 | Prasad | ................... | G06T 5/007 |

* cited by examiner

SYSTEM AND METHOD FOR CALIBRATION BETWEEN COORDINATE SYSTEMS OF 3D CAMERA AND MEDICAL IMAGING APPARATUS AND APPLICATION THEREOF

CROSS-REFERENCE TO RELATED APPLICATIONS

This application claims the benefit of Chinese Patent Application No. 201910506016.2 filed on Jun. 12, 2019, the disclosure of which is herein incorporated by reference in its entirety.

TECHNICAL FIELD

The present invention relates to the medical imaging field, and in particular, to a system and a method for calibration between a coordinate system of a three-dimensional (3D) camera and a coordinate system of a medical imaging apparatus, a specific application of the calibration, and a computer-readable storage medium capable of implementing the calibration method and the application.

BACKGROUND

In the conventional medical imaging process, an imaging device is scanned through a medical imaging apparatus in order to acquire image information of a patient to be scanned or a part to be scanned. However, if a user wishes to obtain more intuitive, accurate and effective feature information, a video or image-based camera needs to be further incorporated. For example, 3D cameras are incorporated in computed tomography (CT) to allow CT users to perform a variety of intuitive, accurate and effective operations, such as estimation of a scanning range, displaying and adjusting the scanning range, and estimation of a patient's body width, etc. In addition, safety-related operations, such as detection of movements of a patient as well as collision prediction prior to movement of a scanning table, can be provided to CT users.

However, the medical imaging apparatus and the camera have different coordinate systems. Accordingly, transformation needs to be implemented between the two coordinate systems. Such transformation is usually referred to in the art as calibration. Both transformation and calibration require a large number of data sets to form a calibration matrix. By means of the calibration matrix, the information acquired through the camera can then be converted to be used in the medical imaging apparatus for subsequent processing.

Existing transformation and calibration techniques both involve medical imaging scanning. A specific example would be that CT scanning is performed on a calibration object on the scanning table to obtain a set of data, and meanwhile, the calibration object is imaged through the 3D camera to obtain another set of data; afterwards, a transformation relationship is calculated based on the two sets of data. In another example, U.S. Pat. No. 9,633,435B2 with the publication date of Mar. 30, 2017 has disclosed a method for calibrating an RGB-D sensor and a medical imaging scanner using a transformation matrix, where the medical imaging scanner obtains a first data set through imaging scanning, while data sensed by the RGB-D sensor is used as a second data set, and the transformation matrix is obtained based on the two data sets.

The involvement of medical imaging scanning results in additional radiation in the transformation or calibration process, which is definitely undesirable from the perspective of radiation safety. The process is also inevitably made more time consuming and requires an operator to control imaging scanning on a console outside a scanning room, which is quite inconvenient. Furthermore, the introduction of a 3D camera that can enable users to implement various operations more intuitively, accurately and effectively is desired.

As a result, an urgent need exists for a new technique solution capable of conveniently and accurately implementing calibration between coordinate systems of a 3D camera and a medical imaging apparatus without radiation.

SUMMARY

The present invention aims to overcome the above and/or other problems in the prior art. By means of the calibration system and method provided in the present invention, data sets required for a calibration matrix can be obtained without medical scanning, and then calibration between coordinate systems of a 3D camera and a medical imaging apparatus can be conveniently and accurately achieved without radiation. Many applications in medical imaging can be conveniently implemented through calibration of the present invention.

According to a first aspect of the present invention, a system for calibration between a coordinate system of a 3D camera and a coordinate system of a medical imaging apparatus is provided, the system comprising: a calibration tool arranged on a scanning table in the medical imaging apparatus, wherein the calibration tool is provided with markers and a reference point, the reference point is aligned with a center of the medical imaging apparatus to serve as an origin of the coordinate system of the medical imaging apparatus, and positions of the markers in the coordinate system of the medical imaging apparatus are calculated according to relative positions of the markers with respect to the reference point; a 3D camera for capturing images of the markers and determining positions of the markers in the coordinate system of the 3D camera based on the captured images; and a calculation device for using the positions of the markers in the coordinate system of the 3D camera as a first data set, using the positions of the markers in the coordinate system of the medical imaging apparatus as a second data set, calculating a calibration matrix between the coordinate system of the 3D camera and the coordinate system of the medical imaging apparatus based on the first data set and the second data set, and performing calibration between the coordinate system of the 3D camera and the coordinate system of the medical imaging apparatus using the calibration matrix.

The aforementioned system completely does not require imaging scanning in the process of calculating a calibration matrix. Positions of the markers on the calibration tool in the coordinate system of the medical imaging apparatus can be obtained through pure calculation, and meanwhile, positions of the markers on the calibration tool in the coordinate system of the 3D camera are obtained through the 3D camera, and finally, the calibration matrix between the coordinate system of the 3D camera and the coordinate system of the medical imaging apparatus is obtained based on the two sets of position data. Since no radiation is involved in the entire process, high radiation safety is achieved; and time is also saved because no imaging scanning is required, and the operator does not need to leave the scanning room to control imaging scanning over the console. In addition, positions of the markers in the coordinate system of the medical imaging apparatus are calculated according to relative positions of the markers with respect to the reference point, which also significantly improves the accuracy of calibration between the coordinate systems of the 3D camera and the medical imaging apparatus.

Preferably, laser beams emitted by a laser lamp in the medical imaging apparatus intersect the reference point at the center of the medical imaging apparatus.

Thus, the system for calibration between coordinate systems of a 3D camera and a medical imaging apparatus according to the present invention completes the benchmarking process of the calibration tool by means of the laser lamp, which can position the calibration tool more intuitively compared with the conventional method of obtaining the position of the calibration tool using imaging scanning.

More preferably, in the calibration system according to the present invention, the calibration tool is further provided with auxiliary lines intersecting at the reference point, the laser beams comprise a first beam and a second beam, and the two auxiliary lines coincide with the first beam and the second beam respectively.

Thus, the aforementioned auxiliary lines are introduced to facilitate alignment of the reference point on the calibration tool with the center of the medical imaging apparatus.

Preferably, in the aforementioned system for calibration between a coordinate system of a 3D camera and a coordinate system of a medical imaging apparatus, the calibration matrix comprises a rotation matrix, a translation matrix, and a scaling matrix.

Since the size of an object acquired in the 3D camera may be different from the physical size of the object in the real world, the aforementioned scaling matrix is introduced to further ensure the accuracy of calibration between the coordinate systems of the 3D camera and the medical imaging apparatus.

Preferably, the aforementioned system for calibration between a coordinate system of a 3D camera and a coordinate system of a medical imaging apparatus may further comprise: a checking unit for checking the calibration matrix through comparing a third data set with a fourth data set, wherein the third data set is positions of the markers in the coordinate system of the medical imaging apparatus which are obtained by calibrating the positions of the markers acquired from the 3D camera through the calibration matrix, and the fourth data set is actual positions of the markers in the coordinate system of the medical imaging apparatus.

Specifically, in the checking unit, a mean absolute error between the third data set and the fourth data set may be calculated, and the mean absolute error may be compared with a threshold.

The aforementioned checking unit helps an engineer or a user to easily check whether calibration between the coordinate systems of the 3D camera and the medical imaging apparatus has been completed and whether the calibration meets required accuracy requirements.

Preferably, in the aforementioned system for calibration between a coordinate system of a 3D camera and a coordinate system of a medical imaging apparatus, shapes and sizes of the markers may further be set, and the positions of the markers in the coordinate system of the medical imaging apparatus may be calculated according to the relative positions of the markers with respect to the reference point and the set shapes and sizes.

For the aforementioned markers on the calibration tool, the size and number thereof both can be set according to needs. Moreover, the markers may have various shapes, and the shapes of the markers may be designed to be accurately captured by the 3D camera so as to generate marker positions thereof in the coordinate system of the 3D camera more accurately. According to a second aspect of the present invention, a method for calibration between a coordinate system of a 3D camera and a coordinate system of a medical imaging apparatus is provided, wherein a calibration tool is arranged on a scanning table in the medical imaging apparatus, and the calibration tool is provided with a reference point and markers, the method comprising: aligning the reference point with a center of the medical imaging apparatus to serve as an origin of the coordinate system of the medical imaging apparatus; calculating positions of the markers in the coordinate system of the medical imaging apparatus according to relative positions of the markers with respect to the reference point; capturing images of the markers through the 3D camera and determining positions of the markers in the coordinate system of the 3D camera based on the captured images; using the positions of the markers in the coordinate system of the 3D camera as a first data set, and meanwhile using the positions of the markers in the coordinate system of the medical imaging apparatus as a second data set, and calculating a calibration matrix between the coordinate system of the 3D camera and the coordinate system of the medical imaging apparatus based on the first data set and the second data set; and performing calibration between the coordinate system of the 3D camera and the coordinate system of the medical imaging apparatus using the calibration matrix.

Preferably, in the aforementioned method, laser beams emitted by a laser lamp in the medical imaging apparatus are made to intersect the reference point at the center of the medical imaging apparatus.

More preferably, the calibration tool is further provided with auxiliary lines intersecting at the reference point, the laser beams comprise a first beam and a second beam, and the two auxiliary lines are made coincide with the first beam and the second beam respectively.

Preferably, in the aforementioned method for calibration between a coordinate system of a 3D camera and a coordinate system of a medical imaging apparatus, the calibration matrix comprises a rotation matrix, a translation matrix, and a scaling matrix.

Preferably, the aforementioned method may further comprise: checking the calibration matrix through comparing a third data set with a fourth data set, wherein the third data set is positions of the markers in the coordinate system of the medical imaging apparatus which are obtained by calibrating the positions of the markers acquired from the 3D camera through the calibration matrix, and the fourth data set is actual positions of the markers in the coordinate system of the medical imaging apparatus.

Specifically, in the step of checking the calibration matrix, a mean absolute error between the third data set and the fourth data set may be calculated, and the mean absolute error may be compared with a threshold.

Preferably, in the aforementioned method for calibration between a coordinate system of a 3D camera and a coordinate system of a medical imaging apparatus, in the step of calculating positions of the markers in the coordinate system of the medical imaging apparatus, shapes and sizes of the markers may be set, and the positions of the markers in the coordinate system of the medical imaging apparatus may be calculated according to the relative positions of the markers with respect to the reference point and the set shapes and sizes.

The aforementioned method corresponds to the system for calibration between a coordinate system of a 3D camera and a coordinate system of a medical imaging apparatus according to the present invention, and can achieve all technical effects that can be achieved by the system.

The medical imaging apparatus according to the present invention may comprise a CT apparatus, a magnetic resonance (MR) apparatus, a positron emission computed tomography (PET) apparatus, or a combination of the apparatuses.

According to a third aspect of the present invention, a scanning positioning method for a medical imaging apparatus is provided, the method comprising: acquiring a 3D image of a patient to be scanned on a scanning table of the medical imaging apparatus through a 3D camera; identifying the acquired 3D image to obtain human anatomical structure information of the patient to be scanned; determining a range to be scanned in the 3D image based on the human anatomical structure information; and calibrating the range to be scanned in a coordinate system of the 3D camera to a coordinate system of the medical imaging apparatus through the method for calibration between a coordinate system of a 3D camera and a coordinate system of a medical imaging apparatus according to the present invention.

According to a fourth aspect of the present invention, a method for displaying a scanning range is provided, the method comprising: acquiring key points of the scanning range through a 3D camera; calibrating positions of the key points in a coordinate system of the 3D camera to positions of the key points in a coordinate system of a medical imaging apparatus through the method for calibration between a coordinate system of a 3D camera and a coordinate system of a medical imaging apparatus according to the present invention; acquiring positions of a start point and an end point of the scanning range in the coordinate system of the medical imaging apparatus according to a predetermined distance between the start point and the end point and the positions of the key points in the coordinate system of the medical imaging apparatus; and displaying pixel positions of the start point and the end point of the scanning range in a screen of the 3D camera which are obtained through an inverse operation of the calibration matrix.

According to a fifth aspect of the present invention, a method for predicting collision of a human body is provided, the method comprising: acquiring point cloud data of the human body through a 3D camera; calibrating the point cloud data to a coordinate system of a medical imaging apparatus through the method for calibration between a coordinate system of a 3D camera and a coordinate system of a medical imaging apparatus according to the present invention; and predicting a possibility of collision between the human body and a scanning gantry through comparing positions of the point cloud data in the coordinate system of the medical imaging apparatus with a position of the scanning gantry in the coordinate system of the medical imaging apparatus.

The three aspects described above are specific applications according to the present invention for the calibration between coordinate systems of a 3D camera and a medical imaging apparatus in the medical imaging field. However, it should be clear to those skilled in the art that the calibration technique according to the present invention can further be widely applied in many other occasions.

According to a sixth aspect of the present invention, a computer-readable storage medium is provided, the computer-readable storage medium having coded instructions recorded thereon, wherein when the instructions are executed, the aforementioned method for calibration between a coordinate system of a 3D camera and a coordinate system of a medical imaging apparatus and various applications thereof can be implemented.

Other features and aspects will become clear through the following detailed description, accompanying drawings, and claims.

BRIEF DESCRIPTION OF THE DRAWINGS

The present invention may be better understood by describing exemplary embodiments of the present invention with reference to accompanying drawings, wherein.

DETAILED DESCRIPTION

Specific implementation manners of the present invention will be described in the following. It should be noted that during the specific description of the implementation manners, it is impossible to describe all features of the actual implementation manners in detail in this description for the sake of brief description. It should be understood that in the actual implementation of any of the implementation manners, as in the process of any engineering project or design project, a variety of specific decisions are often made in order to achieve the developer's specific objectives and meet system-related or business-related restrictions, which will vary from one implementation manner to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The words "first," "second" and similar words used in the description and claims of the patent application of the present invention do not denote any order, quantity or importance, but are merely intended to distinguish between different constituents. "One," "a" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

According to an embodiment of the present invention, a system for calibration between a coordinate system of a 3D camera and a coordinate system of a medical imaging apparatus is provided.

Figure 1:
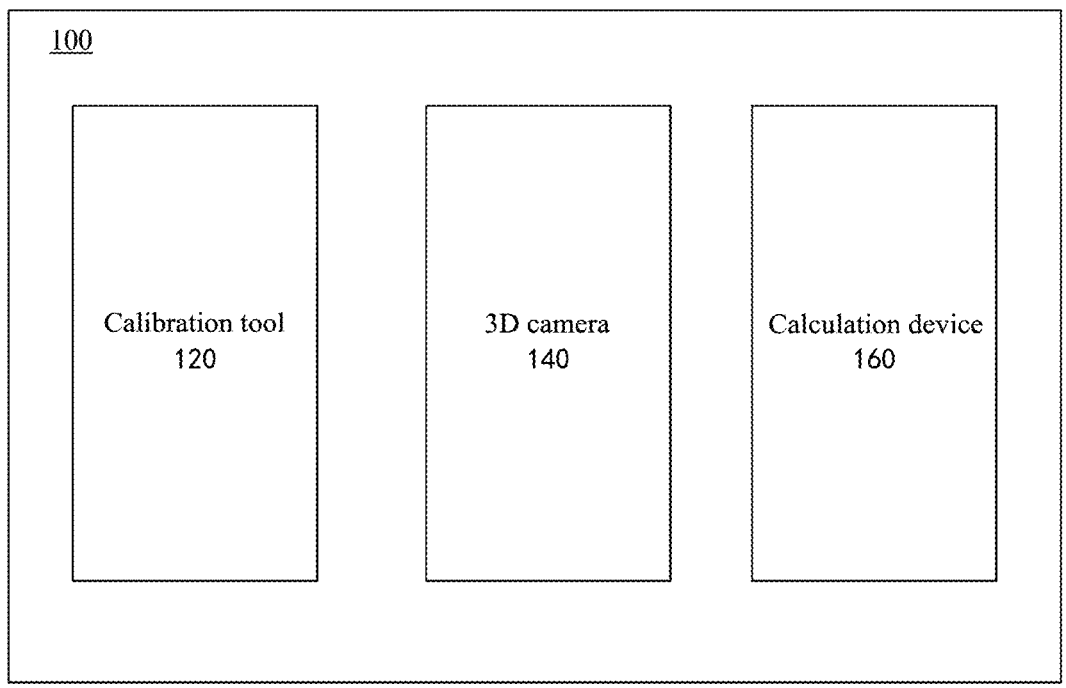
FIG. 1 is a schematic block diagram of a system for calibration between a coordinate system of a 3D camera and a coordinate system of a medical imaging apparatus according to an exemplary embodiment of the present invention.
Figure 2:
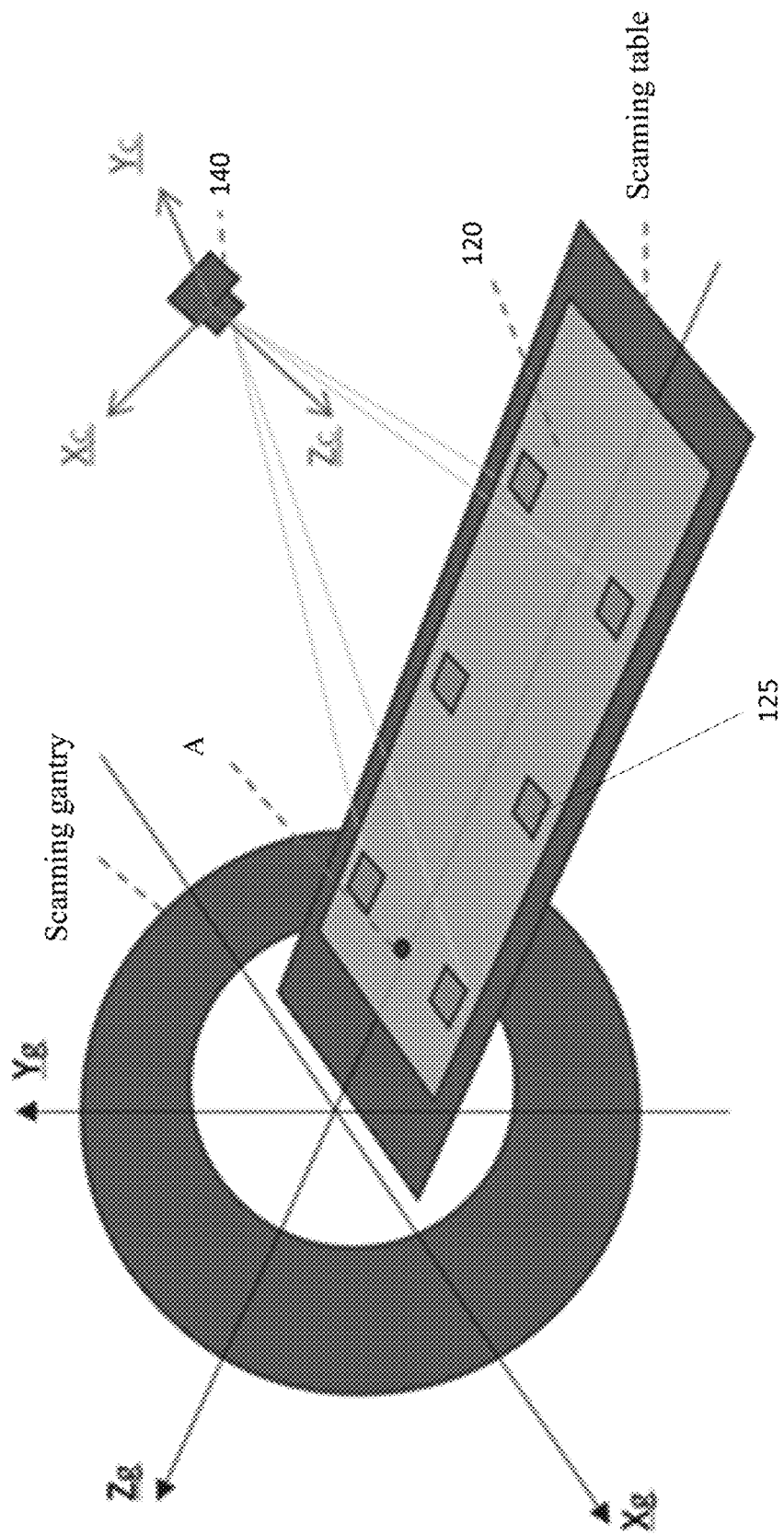
FIG. 2 is a schematic operational diagram of a system for calibration between a coordinate system of a 3D camera and a coordinate system of a medical imaging apparatus according to an exemplary embodiment of the present invention.

FIG. 1 is a schematic block diagram of a system 100 for calibration between a coordinate system of a 3D camera and a coordinate system of a medical imaging apparatus according to an exemplary embodiment of the present invention. The system 100 includes a calibration tool 120, a 3D camera 140, and a calculation device 160. FIG. 2 is a schematic operational diagram of the system 100, where Xc, Yc and Zc represent a coordinate system of the 3D camera 140, and Xg, Yg and Zg represent a coordinate system of a medical imaging apparatus.

With reference to FIG. 2, the calibration tool 120 is arranged on a scanning table in the medical imaging apparatus. Markers 125 and a reference point A are provided on the calibration tool 120. The reference point A is aligned with a center of the medical imaging apparatus to serve as an origin (0, 0, 0) (namely, an intersection of Xg, Yg, and Zg axes) of the coordinate system of the medical imaging apparatus. Then, positions of the markers 125 in the coordinate system of the medical imaging apparatus are calculated according to relative positions of the markers 125 with respect to the reference point A (namely, the origin of the coordinate system of the medical imaging apparatus).

The 3D camera 140 shown in FIG. 1 and FIG. 2 is used for capturing images of the markers 125 and determining positions of the markers 125 in the coordinate system of the 3D camera 140 based on the captured images.

The calculation device 160 shown in FIG. 1 implements the following calculation function on the basis of the aforementioned two sets of position data: using the positions of the markers 125 in the coordinate system of the 3D camera 140 as a first data set, using the positions of the markers 125 in the coordinate system of the medical imaging apparatus as a second data set, calculating a calibration matrix M between the coordinate system of the 3D camera 140 and the coordinate system of the medical imaging apparatus based on the first data set and the second data set, and performing calibration between the coordinate system of the 3D camera 140 and the coordinate system of the medical imaging apparatus using the calibration matrix M.

The aforementioned system does not require imaging scanning at all in the process of calculating a calibration matrix. Positions of the markers 125 on the calibration tool 120 in the coordinate system of the medical imaging apparatus can be obtained through the calculation device 160 through pure calculation. Together with positions of the markers 125 in the coordinate system of the 3D camera 140 which are obtained through the 3D camera 140, the calibration matrix M between the coordinate system of the 3D camera 140 and the coordinate system of the medical imaging apparatus can be obtained based on the two sets of position data. The entire process does not require any radiation, achieving quite high radiation safety; time is also saved because no imaging scanning is required, and the operator would not need to leave the scanning room to control imaging scanning over the console. In addition, positions of the markers 125 in the coordinate system of the medical imaging apparatus are calculated according to relative positions of the markers 125 with respect to the reference point A, which also significantly improves the accuracy of calibration between the coordinate systems of the 3D camera 140 and the medical imaging apparatus.

Furthermore, laser beams emitted by a laser lamp in the medical imaging apparatus intersect the reference point A at the center of the medical imaging apparatus.

Figure 3:
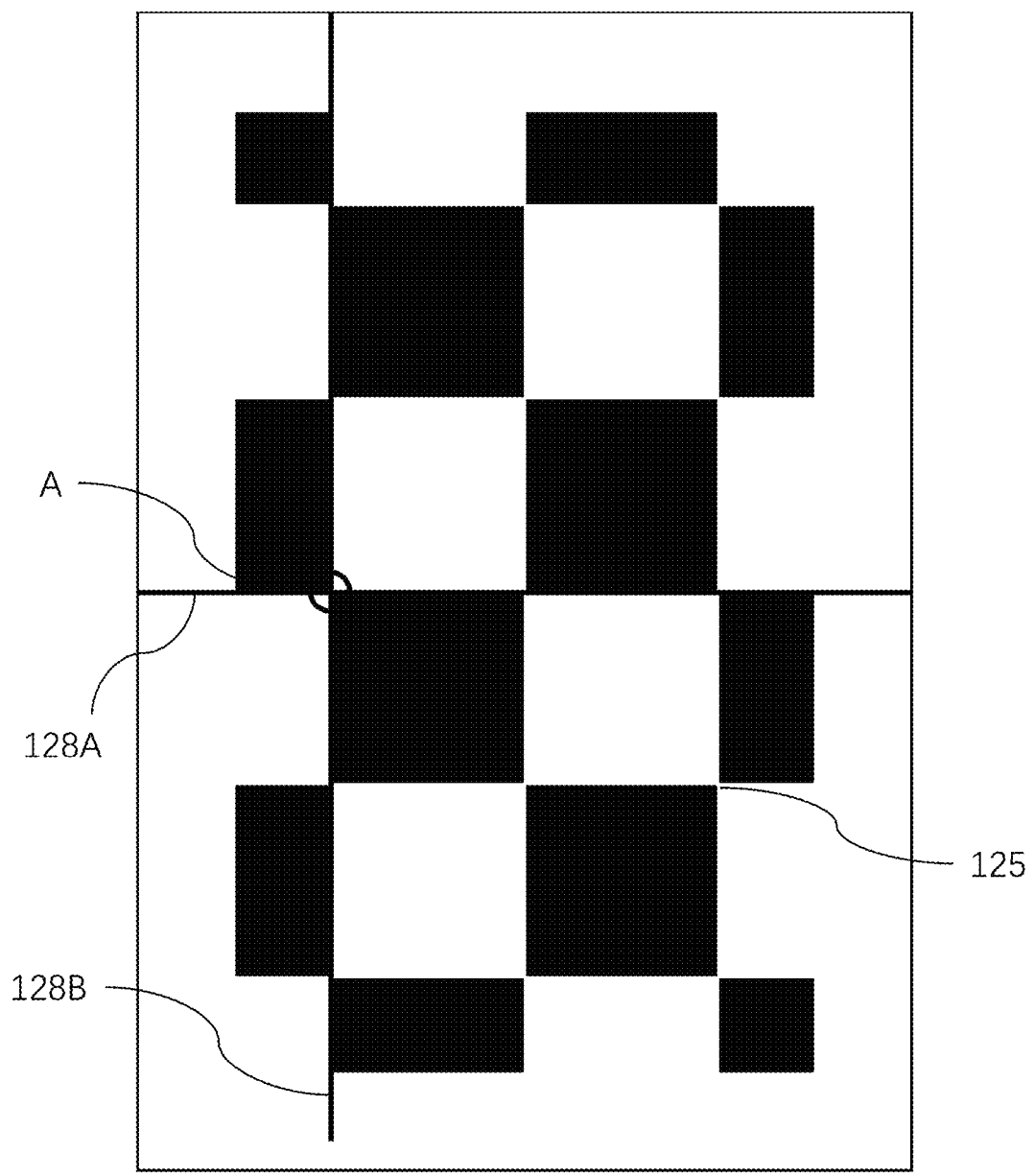
FIG. 3 is a schematic diagram of a calibration tool in the system shown in FIG. 2.

FIG. 3 is a schematic diagram of the calibration tool 120 in the aforementioned system, which is specifically represented in the form of pixels of alternate black and white squares.

As shown in FIG. 3, the calibration tool 120 is further provided with auxiliary lines 128A and 128B intersecting at the reference point A. The auxiliary lines 128A and 128B may preferably be perpendicular to each other in the plane of the calibration tool 120 as shown in FIG. 3, namely, in the directions of the Xg axis and the Zg axis shown in FIG. 2. The laser beams emitted by the laser lamp may include a first beam and a second beam. The calibration tool 120 may be moved so that the auxiliary lines 128A and 128B coincide with the first beam and the second beam respectively, and thus the reference point A can be aligned with the center of the medical imaging apparatus more conveniently.

In this way, the reference point A is intuitively and easily determined as the origin (0, 0, 0) of the coordinate system of the medical imaging apparatus. FIG. 3 further shows the positions of the markers 125. In the figure, an intersection of each black square and each white square corresponds to one marker 125.

Although it is described above that the reference point A is aligned with the center of the medical imaging apparatus through the auxiliary lines 128A and 128B, those skilled in the art should know that the reference point A can be aligned with the center of the medical imaging apparatus even without the auxiliary lines 128A and 128B.

Figure 4:
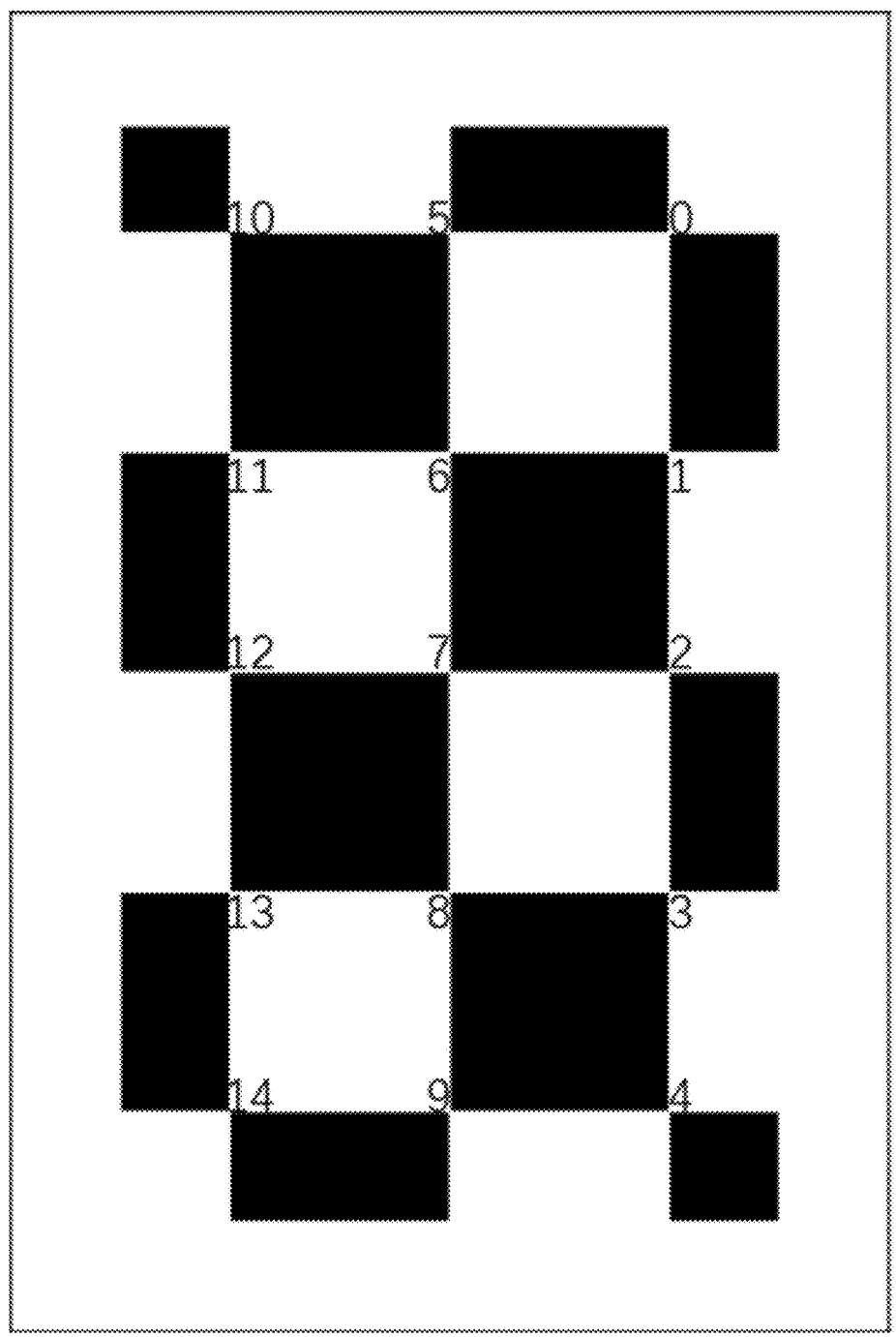
FIG. 4 illustrates pixel positions of markers on the calibration tool in the system shown in FIG. 2.

Furthermore, referring to FIG. 4, FIG. 4 shows a pixel position of each marker 125 on the calibration tool 120. The pixel position is a pixel position of the marker 125 in the coordinate system of the 3D camera, which will be described in detail below and will not be elaborated at this point.

An intersection of each black square and each white square in FIG. 4 corresponds to one marker 125. The number labeled next to the marker is a relative distance of the marker to the reference point A, and a coordinate position of each marker 125 in the coordinate system of the medical imaging apparatus can be obtained according to the relative distance.

In view of the above, the system 100 for calibration between a coordinate system of a 3D camera and a coordinate system of a medical imaging apparatus in the present invention performs benchmarking with the calibration tool 120 by means of the laser lamp. As compared with the conventional method of obtaining the position of the calibration tool using imaging scanning, this method can position the calibration tool more intuitively, has higher radiation safety, and saves time as the operator would not have to control imaging scanning outside the scanning room.

Furthermore, the auxiliary lines 128A and 128B are further introduced as shown in FIG. 3, so as to facilitate faster alignment of the reference point A on the calibration tool 120 with the center of the medical imaging apparatus.

It should be particularly noted that although six markers 125 on the calibration tool 120 in FIG. 2 are shown, the number of the markers 125 may be set to any number according to needs in practice. Moreover, although the markers 125 in FIG. 2 are rectangular, the sizes and shapes of the markers 125 may also be set according to needs in practice. The markers 125 may have various shapes, so that the shapes of the markers 125 may be designed to be accurately captured by the 3D camera 140 more easily so as to generate marker positions of the markers 125 in the coordinate system of the 3D camera 140. Once the shapes and sizes of the markers 125 are set according to needs, the set shapes and sizes may also be considered in addition to the relative positions of the markers 125 with respect to the reference point A when the positions of the markers 125 in the coordinate system of the medical imaging apparatus are calculated.

In view of this, no special knowledge is needed in operating the calibration tool 120, and the markers 125 provided on the calibration tool 120 may have various shapes, thereby allowing high convenience to a user and facilitating updates. The operator only needs to enter the positions, shapes, and sizes of the markers 125, so that the calibration can be implemented automatically.

In addition, in the calibration system 100, the 3D camera 140 captures depth images, infrared images, and RGB images of the markers 125, and may process the infrared images and the RGB images using, for example, an open-source method in a cross-platform computer vision library (OpenCV), so as to obtain pixel positions of the markers 125 in the coordinate system of the 3D camera, as shown in FIG. 4.

Furthermore, depth information of the markers may be obtained from the depth images of the markers 125. Thus, a three-dimensional position (Xc, Yc, Zc) of each marker 125 in the coordinate system of the 3D camera can be determined based on the depth information and the previously obtained pixel positions of the markers 125 in the coordinate system of the 3D camera.

In the system 100 for calibration between a coordinate system of a 3D camera and a coordinate system of a medical imaging apparatus according to the present invention, the calibration matrix M first includes a rotation matrix r and a translation matrix t. The two matrices already can implement calibration between the coordinate system of the 3D camera 140 and the coordinate system of the medical imaging apparatus. However, since the size of an object acquired in the 3D camera 140 may be different from the physical size of the object in the real world, according to the present invention, the calibration matrix M further particularly includes a scaling matrix s, so as to exclude an object whose size is incorrect compared with the real physical size. In this way, the calibration matrix M is undoubtedly enhanced, and better calibration accuracy can be obtained.

Figure 5:
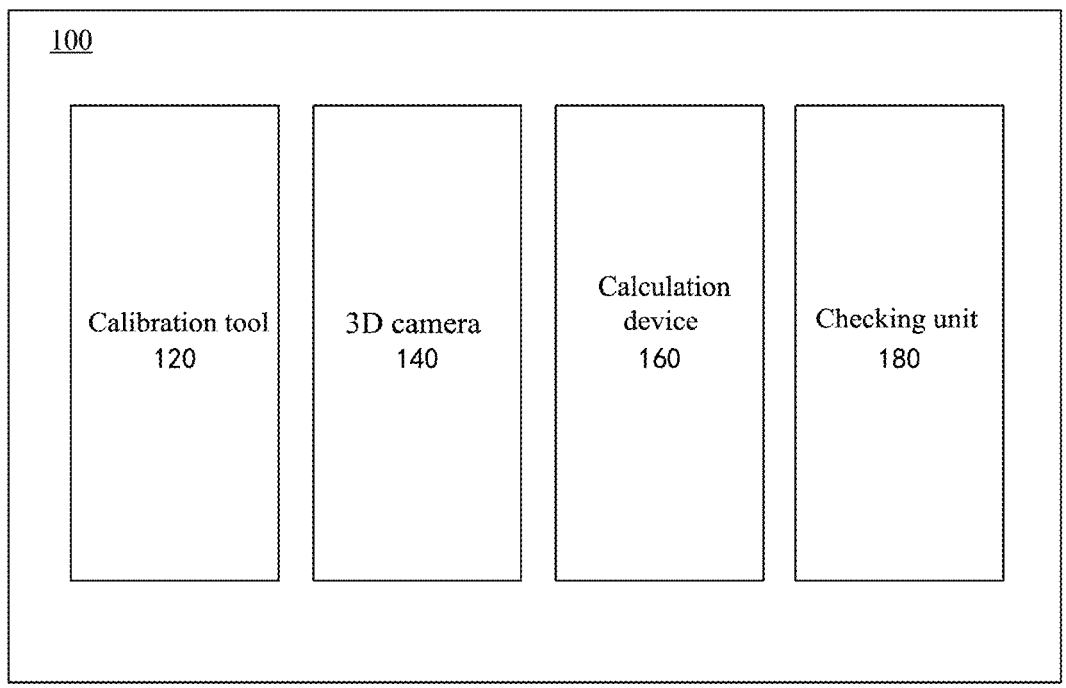
FIG. 5 is a schematic block diagram of a variant embodiment of the system shown in FIG. 1.

Furthermore, referring to FIG. 5, the system 100 for calibration between a coordinate system of a 3D camera and a coordinate system of a medical imaging apparatus according to the present invention may further include a checking unit 180.

The checking unit 180 first calibrates positions of the markers 125 obtained from the 3D camera 140 to positions P in the coordinate system of the medical imaging apparatus through the calibration matrix M, and then compares the calibrated positions P with actual positions P of the markers 125 in the coordinate system of the medical imaging apparatus. The actual positions P of the markers 125 in the coordinate system of the medical imaging apparatus may be determined by, for example, laser benchmarking. The checking unit 180 can check the calibration matrix M through the aforementioned comparison.

In the aforementioned comparison, specifically, for example, a mean absolute error between P' and P may be calculated, and the mean absolute error may be compared with a preset threshold, so as to judge whether the calibration accuracy of the calibration matrix M is expected. The preset threshold may be determined according to factors such as the work requirements and the environment.

The aforementioned checking unit 180 helps an engineer or a user to easily check whether calibration between the coordinate systems of the 3D camera 140 and the medical imaging apparatus has been completed and whether the calibration meets required accuracy requirements.

The medical imaging apparatus in the present invention may include a variety of apparatuses, specifically, for example, a CT apparatus, an MR apparatus, and a PET apparatus, and may further include various combinations of these apparatuses.

Figure 6:
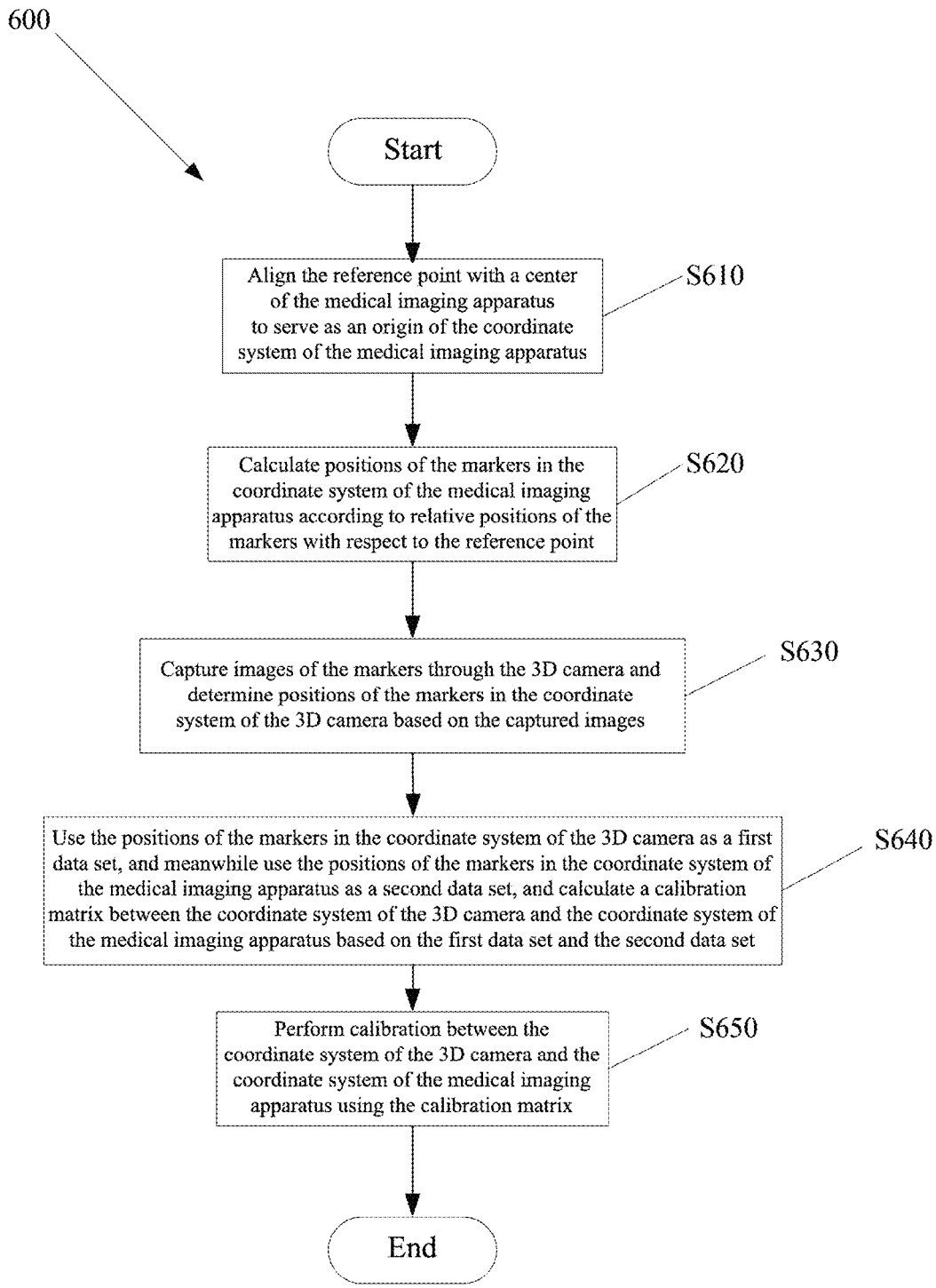
FIG. 6 is a flowchart of a method for calibration between a coordinate system of a 3D camera and a coordinate system of a medical imaging apparatus according to an exemplary embodiment of the present invention.

According to an embodiment of the present invention, a method 600 for calibration between a coordinate system of a 3D camera and a coordinate system of a medical imaging apparatus is further provided accordingly, as shown in FIG. 6. The method 600 includes steps S610 to S650. With reference to FIG. 2 again, a calibration tool 120 is arranged on a scanning table in the medical imaging apparatus, and the calibration tool 120 is provided with a reference point A and markers 125.

Referring to FIG. 6, step S610: align the reference point A with a center of the medical imaging apparatus to serve as an origin of the coordinate system of the medical imaging apparatus.

For example, laser beams emitted by a laser lamp in the medical imaging apparatus may be made to intersect the reference point A at the center of the medical imaging apparatus. In this way, in the aforementioned step S610, the reference point A is aligned with the center of the medical imaging apparatus.

With further reference to FIG. 3, auxiliary lines 128A and 128B intersecting at the reference point A may further be provided on the calibration tool 120, for example. The laser beams emitted by the laser lamp may include a first beam and a second beam. The calibration tool 120 may be moved so that the auxiliary lines 128A and 128B coincide with the first beam and the second beam respectively, and thus the reference point A can be aligned with the center of the medical imaging apparatus more conveniently.

Referring back to FIG. 6, step S620: calculate positions of the markers 125 in the coordinate system of the medical imaging apparatus according to relative positions of the markers 125 with respect to the reference point A.

As shown in FIG. 4, an intersection of each black square and each white square corresponds to one marker 125, the number labeled next to the marker is a relative distance of the marker to the reference point A, and a coordinate position of each marker 125 in the coordinate system of the medical imaging apparatus can be obtained according to the relative distance.

In addition, in step S620, shapes and sizes of the markers 125 can be set. Moreover, once the shapes and sizes of the markers 125 are set, the positions of the markers 125 in the coordinate system of the medical imaging apparatus are calculated according to the relative positions of the markers 125 with respect to the reference point A and the set shapes and sizes.

Still referring back to FIG. 6, step S630: capture images of the markers 125 through the 3D camera 140 shown in FIG. 2 and determine positions of the markers 125 in the coordinate system of the 3D camera 140 based on the captured images.

Specifically, the 3D camera 140 captures depth images, infrared images, and RGB images of the markers 125, and may process the infrared images and the RGB images of the markers 125 using an open-source method in an OpenCV, so as to obtain pixel positions of the markers 125 in the coordinate system of the 3D camera, as shown in FIG. 4.

The depth images of the markers 125 may further be processed to obtain depth information of the markers 125, where the depth information corresponds to the pixel positions of the markers 125 in the coordinate system of the 3D camera. Thus, three-dimensional positions (Xc, Yc, Zc) of the markers 125 in the coordinate system of the 3D camera can be determined based on the depth information and the pixel positions of the markers 125 in the coordinate system of the 3D camera.

It should be noted that although step S630 is described by using the open-source method in an OpenCV as an example, those skilled in the art should know that this step may also be implemented using other image processing techniques, and not limited to the open-source method in an OpenCV.

Referring back to FIG. 6, step S640: use the positions of the markers 125 in the coordinate system of the 3D camera 140 as a first data set, and meanwhile use the positions of the markers 125 in the coordinate system of the medical imaging apparatus as a second data set, and calculate a calibration matrix M between the coordinate system of the 3D camera 140 and the coordinate system of the medical imaging apparatus based on the first data set and the second data set.

With reference to FIG. 2, as the scanning table moves in the Zg and Yg directions, when the calibration tool 120 enters the field of view (FOV) of the 3D camera 140, pixel positions of the markers 125 on the calibration tool 120 are determined based on RGB images and infrared images, and coordinates of the markers 125 in the coordinate system of the 3D camera 140 may be determined based on the pixel positions together with depth information obtained from depth images, so as to serve as the first data set; and positions of the markers 125 in the coordinate system of the medical imaging apparatus may be determined based on the movement of the scanning table and relative positions of the markers 125 with respect to the reference point A, so as to serve as the second data set.

According to the present invention, the calibration matrix M may specifically include a rotation matrix r, a translation matrix t, and a scaling matrix s. As previously described, the introduction of the scaling matrix s can exclude an object whose size is incorrect compared with the real physical size.

Referring back to FIG. 6 again, finally, step S650: implement calibration between the coordinate system of the 3D camera 140 and the coordinate system of the medical imaging apparatus using the calibration matrix M.

Figure 7:
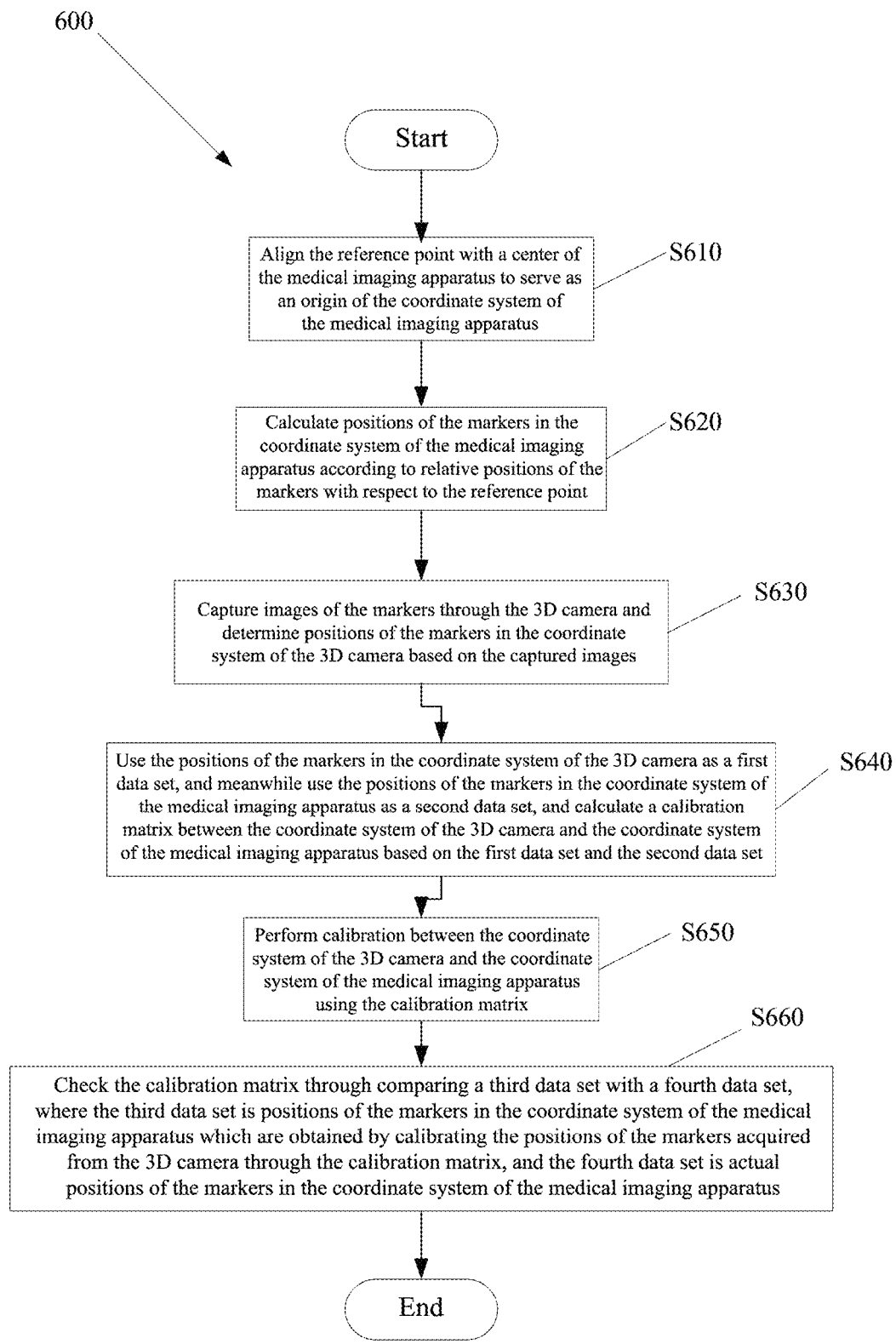
FIG. 7 is a flowchart of a variant embodiment of the method shown in FIG. 6.

Furthermore, referring to FIG. 7, the calibration method 600 according to the present invention may further include step S660: checking the calibration matrix M through comparing a third data set with a fourth data set.

Specifically, in step S660, first, positions of the markers 125 obtained from the 3D camera 140 are calibrated to positions P' (the third data set) in the coordinate system of the medical imaging apparatus through the calibration matrix M, and then, the calibrated positions P' are compared with actual positions P (the fourth data set) of the markers 125 in the coordinate system of the medical imaging apparatus. The actual positions P of the markers 125 in the coordinate system of the medical imaging apparatus may be determined by, for example, laser benchmarking. The calibration matrix M can be checked through the aforementioned comparison.

For the aforementioned comparison, specifically, for example, a mean absolute error between P' and P may be calculated, and the mean absolute error may be compared with a preset threshold, so as to judge whether the calibration accuracy of the calibration matrix M is expected. The preset threshold may be determined according to factors such as the work requirements and the environment.

As previously described, the medical imaging apparatus may include a variety of apparatuses, specifically, for example, a CT apparatus, an MR apparatus, and a PET apparatus, and may further include various combinations of these apparatuses.

The aforementioned method 600 and various alternative embodiments and examples thereof correspond to the system 100 for calibration between a coordinate system of a 3D camera and a coordinate system of a medical imaging apparatus according to the present invention. Many design details of the system 100 also apply to the method 600 and various alternative embodiments thereof, and the method 600 and various alternative embodiments thereof can achieve all technical effects that can be achieved by the system 100.

The aforementioned system and method for calibration between coordinate systems of a 3D camera and a medical imaging apparatus in the present invention can be widely applied in many occasions in the medical imaging field.

Specifically, for example, according to the present invention, a scanning positioning method for a medical imaging apparatus is further provided, the method including: acquiring a 3D image of a patient to be scanned on a scanning table of the medical imaging apparatus through a 3D camera; identifying the acquired 3D image to obtain human anatomical structure information of the patient to be scanned; determining a range to be scanned in the 3D image based on the human anatomical structure information; and calibrating the range to be scanned in a coordinate system of the 3D camera to a coordinate system of the medical imaging apparatus through the method for calibration between a coordinate system of a 3D camera and a coordinate system of a medical imaging apparatus according to the present invention.

For another example, according to the present invention, a method for displaying a scanning range is further provided, including: acquiring key points of the scanning range through a 3D camera; calibrating positions of the key points in a coordinate system of the 3D camera to positions of the key points in a coordinate system of a medical imaging apparatus through the method for calibration between a coordinate system of a 3D camera and a coordinate system of a medical imaging apparatus according to the present invention; acquiring positions of a start point and an end point of the scanning range in the coordinate system of the medical imaging apparatus, according to a predetermined distance between the start point and the end point and the positions of the key points in the coordinate system of the medical imaging apparatus; and displaying pixel positions of the start point and the end point of the scanning range in a screen of the 3D camera which are obtained through an inverse operation of the calibration matrix.

For still another example, according to the present invention, a method for predicting collision of a human body is provided, including: acquiring point cloud data of the human body through a 3D camera; calibrating the point cloud data to a coordinate system of a medical imaging apparatus through the method for calibration between a coordinate system of a 3D camera and a coordinate system of a medical imaging apparatus according to the present invention; and predicting a possibility of collision between the human body and a scanning gantry through comparing positions of the point cloud data in the coordinate system of the medical imaging apparatus with a position of the scanning gantry in the coordinate system of the medical imaging apparatus.

The three examples described above are merely some applications according to the present invention of the calibration between coordinate systems of a 3D camera and a medical imaging apparatus in the medical imaging field. Those skilled in the art should know that the calibration technique according to the present invention can further be widely applied in many other occasions. In these specific applications, since the calibration between coordinate systems of a 3D camera and a medical imaging apparatus according to the present invention is employed, better effects can be obtained more conveniently and quickly based on more accurate data.

According to an embodiment of the present invention, a computer-readable storage medium is further provided, the computer-readable storage medium having coded instructions recorded thereon, where when the instructions are executed, the aforementioned method 600 for calibration between a coordinate system of a 3D camera and a coordinate system of a CT system and various variants and extensions thereof can be implemented, and the aforementioned various applications implemented using the calibration between coordinate systems of a 3D camera and a medical imaging apparatus in the present invention can also be implemented. The computer-readable storage medium may include a hard disk drive, a floppy disk drive, a CD-read/write (CD-R/W) drive, a digital versatile disc (DVD) drive, a flash drive, and/or a solid-state storage device. The computer-readable storage medium may be installed in a medical imaging apparatus, or may be installed in a separate control apparatus or computer that remotely controls the medical imaging apparatus.

Up to now, the system and method for calibration between a coordinate system of a 3D camera and a coordinate system of a medical imaging apparatus according to the present invention, a specific application of the calibration, and a computer-readable storage medium capable of implementing the calibration method and the application have been described.

The aforementioned system and method for calibration between a coordinate system of a 3D camera and a coordinate system of a medical imaging apparatus according to the present invention completely do not require imaging scanning. Positions of the markers on the calibration tool in the coordinate system of the medical imaging apparatus can be obtained through pure calculation, and meanwhile, positions of the markers on the calibration tool in the coordinate system of the 3D camera are obtained through the 3D camera, and finally, the calibration matrix between the coordinate system of the 3D camera and the coordinate system of the medical imaging apparatus is obtained based on the two sets of position data. Since no radiation is involved in the entire process, high radiation safety is achieved; and time is also saved because no imaging scanning is required, and the operator does not need to leave the scanning room to control imaging scanning on the console. In addition, positions of the markers in the coordinate system of the medical imaging apparatus are calculated according to relative positions of the markers with respect to the reference point, which also significantly improves the accuracy of calibration between the coordinate systems of the 3D camera and the medical imaging apparatus.

The present invention provides a convenient and nonradiative method and system for calibration between a camera and a medical imaging apparatus. In contrast with most existing methods for calibration between a camera and a medical imaging apparatus, the present invention does not need to perform imaging scanning for the calibration tool, but performs benchmarking using the laser lamp in the scanning gantry. This allows all processes to be completed beside the scanning table without performing radiation scanning, which greatly enhances convenience.

Moreover, the present invention enables ordinary users to easily accomplish recalibration, which can save technician resources to a large extent compared with other existing techniques that require professional engineers to perform calibration. The present invention can implement a variety of applications of incorporating a 3D camera into a medical imaging apparatus, where the 3D camera completes all calculations in a coordinate system of the 3D camera or using image pixels. According to the present invention, a calibration matrix is generated to calibrate data from the 3D camera to data in a coordinate system of the medical imaging apparatus, so that the operation of the medical imaging apparatus can be directly guided based on the 3D camera.

In addition, by means of the present invention, an imaging device (particularly, a 3D camera) is introduced into a medical imaging apparatus to provide more intuitive feature presentation. As a result, compared with the use of a depth camera having limits, various intuitive and effective operations can be provided to a user more accurately, so that the work flow is more effective and safer operations can be provided to the user, thereby greatly improving user experience. Moreover, the present invention provides a strong guarantee to the technique of configuring a 3D camera in a scanning room to increase interaction with a user. In addition, if a 3D camera needs to be introduced into a machine, the present invention further helps to obtain an important data source for machine digitization.

Some exemplary embodiments have been described above. However, it should be understood that various modifications can be made to the exemplary embodiments described above without departing from the spirit and scope of the present invention. For example, a suitable result can be achieved if the described techniques are performed in a different order and/or if the components of the described system, architecture, apparatus, or circuit are combined in different manners and/or replaced or supplemented with additional components or equivalents thereof. Accordingly, other embodiments of these modifications shall also fall within the protection scope of the claims.

The invention claimed is:

1. A system for calibration between a coordinate system of a 3D camera and a coordinate system of a medical imaging apparatus, the system comprising:
   a calibration tool arranged on a scanning table in the medical imaging apparatus, wherein the calibration tool is provided with markers and a reference point, the reference point is aligned with a center of the medical imaging apparatus to serve as an origin of the coordinate system of the medical imaging apparatus, and positions of the markers in the coordinate system of the medical imaging apparatus are calculated according to relative positions of the markers with respect to the reference point;
   a 3D camera for capturing images of the markers and determining positions of the markers in the coordinate system of the 3D camera based on the captured images; and
   a calculation device for using the positions of the markers in the coordinate system of the 3D camera as a first data set, using the positions of the markers in the coordinate system of the medical imaging apparatus as a second data set, calculating a calibration matrix between the coordinate system of the 3D camera and the coordinate system of the medical imaging apparatus based on the first data set and the second data set, and performing calibration between the coordinate system of the 3D camera and the coordinate system of the medical imaging apparatus using the calibration matrix, wherein laser beams emitted by a laser in the medical imaging apparatus intersect the reference point at the center of the medical imaging apparatus, wherein the calibration tool is further provided with two auxiliary lines intersecting at the reference point, the laser beams comprise a first beam and a second beam, and the two auxiliary lines coincide with the first beam and the second beam respectively.

2. The system according to claim 1, wherein the calibration matrix comprises a rotation matrix, a translation matrix, and a scaling matrix.

3. The system according to claim 1, wherein the system further comprises:
a checking unit for checking the calibration matrix through comparing a third data set with a fourth data set, wherein
the third data set is positions of the markers in the coordinate system of the medical imaging apparatus which are obtained by calibrating the positions of the markers acquired from the 3D camera through the calibration matrix, and the fourth data set is actual positions of the markers in the coordinate system of the medical imaging apparatus.

4. The system according to claim 3, wherein in the checking unit, a mean absolute error between the third data set and the fourth data set is calculated, and the mean absolute error is compared with a threshold.

5. The system according to claim 1, wherein shapes and sizes of the markers are set, and the positions of the markers in the coordinate system of the medical imaging apparatus are calculated according to the relative positions of the markers with respect to the reference point and the set shapes and sizes.

6. The system according to claim 1, wherein the medical imaging apparatus comprises a CT apparatus, an MR apparatus, a PET apparatus, or a combination of the apparatuses.

7. A method for calibration between a coordinate system of a 3D camera and a coordinate system of a medical imaging apparatus, wherein a calibration tool is arranged on a scanning table in the medical imaging apparatus, and the calibration tool is provided with a reference point and markers, the method comprising:
aligning the reference point with a center of the medical imaging apparatus to serve as an origin of the coordinate system of the medical imaging apparatus;
calculating positions of the markers in the coordinate system of the medical imaging apparatus according to relative positions of the markers with respect to the reference point;
capturing images of the markers through the 3D camera and determining positions of the markers in the coordinate system of the 3D camera based on the captured images;
using the positions of the markers in the coordinate system of the 3D camera as a first data set, and meanwhile using the positions of the markers in the coordinate system of the medical imaging apparatus as a second data set, and calculating a calibration matrix between the coordinate system of the 3D camera and the coordinate system of the medical imaging apparatus based on the first data set and the second data set; and
performing calibration between the coordinate system of the 3D camera and the coordinate system of the medical imaging apparatus using the calibration matrix, wherein laser beams emitted by a laser in the medical imaging apparatus are made to intersect the reference point at the center of the medical imaging apparatus, wherein the calibration tool is further provided with two auxiliary lines intersecting at the reference point, the laser beams comprise a first beam and a second beam, and the two auxiliary lines are made coincide with the first beam and the second beam respectively.

8. The method according to claim 7, wherein the calibration matrix comprises a rotation matrix, a translation matrix, and a scaling matrix.

9. The method according to claim 7, further comprising:
checking the calibration matrix through comparing a third data set with a fourth data set, wherein the third data set is positions of the markers in the coordinate system of the medical imaging apparatus which are obtained by calibrating the positions of the markers acquired from the 3D camera through the calibration matrix, and the fourth data set is actual positions of the markers in the coordinate system of the medical imaging apparatus.

10. The method according to claim 9, wherein in the step of checking the calibration matrix, a mean absolute error between the third data set and the fourth data set is calculated, and the mean absolute error is compared with a threshold.

11. The method according to claim 7, wherein in the step of calculating positions of the markers in the coordinate system of the medical imaging apparatus, shapes and sizes of the markers are set, and the positions of the markers in the coordinate system of the medical imaging apparatus are calculated according to the relative positions of the markers with respect to the reference point and the set shapes and sizes.

12. The method according to claim 7, wherein the medical imaging apparatus comprises a CT apparatus, an MR apparatus, a PET apparatus, or a combination of the apparatuses.

13. A scanning positioning method for a medical imaging apparatus, the method comprising:
acquiring a 3D image of a patient to be scanned on a scanning table of the medical imaging apparatus through a 3D camera;
identifying the acquired 3D image to obtain human anatomical structure information of the patient to be scanned;
determining a range to be scanned in the 3D image based on the human anatomical structure information; and
calibrating the range to be scanned in a coordinate system of the 3D camera to a coordinate system of the medical imaging apparatus through the method according to claim 7.

14. A method for displaying a scanning range, the method comprising:
acquiring key points of the scanning range through a 3D camera;
calibrating positions of the key points in a coordinate system of the 3D camera to positions of the key points in a coordinate system of a medical imaging apparatus through the method according to claim 7;
acquiring positions of a start point and an end point of the scanning range in the coordinate system of the medical imaging apparatus according to a predetermined distance between the start point and the end point and the positions of the key points in the coordinate system of the medical imaging apparatus; and displaying pixel positions of the start point and the end point of the scanning range in a screen of the 3D camera which are obtained through an inverse operation of the calibration matrix.

15. A method for predicting collision of a human body, the method comprising:

acquiring point cloud data of the human body through a 3D camera;

calibrating the point cloud data to a coordinate system of a medical imaging apparatus through the method according to claim 7; and predicting a possibility of collision between the human body and a scanning gantry through comparing positions of the point cloud data in the coordinate system of the medical imaging apparatus with a position of the scanning gantry in the coordinate system of the medical imaging apparatus.

16. A non-transitory computer-readable storage medium, having coded instructions recorded thereon, wherein when the instructions are executed, the method according to claim 7 is implemented.

\* \* \* \* \*